(12) United States Patent
Manzke et al.

(10) Patent No.: US 7,346,143 B2
(45) Date of Patent: Mar. 18, 2008

(54) COMPUTER TOMOGRAPHY SCANNER HAVING AN ADJUSTABLE ROTATIONAL SPEED

(75) Inventors: Robert Manzke, Cambridge, MA (US); Michael Grass, Buchholz in der Nordheide (DE); Udo Van Stevendaal, Ahrensburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 11/573,355

(22) PCT Filed: Aug. 2, 2005

(86) PCT No.: PCT/IB2005/052575

§ 371 (c)(1),
(2), (4) Date: Feb. 7, 2007

(87) PCT Pub. No.: WO2006/018763

PCT Pub. Date: Feb. 23, 2006

(65) Prior Publication Data

US 2007/0183557 A1    Aug. 9, 2007

(30) Foreign Application Priority Data

Aug. 12, 2004  (EP)  .................... 04103882

(51) Int. Cl.
*A61B 6/00* (2006.01)

(52) U.S. Cl. ........................... 378/15; 378/207

(58) Field of Classification Search ............. 378/4–20, 378/207
See application file for complete search history.

(56) References Cited

U.S. PATENT DOCUMENTS

| 4,547,892 A | 10/1985 | Richey et al. |
| 6,954,513 B2* | 10/2005 | Horiuchi ........................ 378/4 |
| 2003/0159508 A1* | 8/2003 | Halsmer ...................... 73/462 |

FOREIGN PATENT DOCUMENTS

| EP | 1 050 272 A1 | 11/2000 |
| WO | 99 07283 A1 | 2/1999 |

OTHER PUBLICATIONS

Grass, M., et al.; Helical cardiac cone beam reconstruction using retrospective ECG gating; 2003; Phys. Med. Biol.; vol. 48; pp. 3069-3084.

Manzke, R., et al.; Adaptive temporal resolution optimization in helical cardiac cone beam CT reconstruction; 2003; Med. Phys.; 30(12)3072-3080.

* cited by examiner

*Primary Examiner*—Courtney Thomas (57) ABSTRACT

The invention relates to a computer tomography scanner comprising a gantry, on the rotor of which one or more displaceable masses are arranged. During rotation of the rotor about a rotation axis, the position of each mass can be changed perpendicular to the rotation axis by means of an adjustment unit. By retaining the rotary momentum of the rotor, the rotational speed is increased when the masses are moved toward the rotation axis, and vice versa. As a result, it is possible to maintain a specific ratio between the heart rate of the examined patient and the rotational speed even if the heart rate of the patient changes during the examination.

20 Claims, 6 Drawing Sheets

COMPUTER TOMOGRAPHY SCANNER HAVING AN ADJUSTABLE ROTATIONAL SPEED

The invention relates to a computer tomography (CT) scanner comprising a rotatable gantry. Such computer tomography scanners are used for example in the medical sector to produce slice or volume images of a patient located in the examination area of the computer tomography scanner. Such a computer tomography scanner has a gantry with a rotor which can rotate about a rotation axis. An X-ray source is usually arranged on the rotor, and an X-ray detector is usually arranged opposite said X-ray source. In order to produce images, an examination object is located in the examination area, and the rotor rotates about said examination object. Depending on the design of the computer tomography scanner, a number of linear, disk-shaped or cube-shaped X-ray images are created, from which slice or volume images can be produced by means of known reconstruction algorithms.

Known computer tomography scanners can also be used to record moving or periodically moving objects, for example the human or animal heart. In this case, it may be necessary for the rotational speed of the rotor to be in a certain ratio to the rate of the beating heart. By way of example, it is disclosed in international patent application WO9907283 that the rotor rotates in a manner non-synchronous to the heart rate, whereas in U.S. Pat. No. 4,547,892 it is disclosed that the rotor rotates in a manner synchronous to the heart rate. However, it has been found that the heart rate of patients can vary considerably during an examination, for example because the heart is diseased, the patient is excited or a contrast agent or medicament is administered to the patient. This means that the respective ratio between rotational speed and heart rate is no longer set, and satisfactory image production is often no longer possible.

It is therefore an object of the present invention to develop a computer tomography scanner by means of which image production is possible even if the heart rate varies.

This object is achieved as claimed in claim 1 by a computer tomography scanner comprising a rotor which can rotate about a rotation axis, at least one mass arranged on the rotor, and an adjustment unit for changing the position of the mass perpendicular to the rotation axis during rotation of the rotor.

On account of its high weight and corresponding size, the rotor has a large moment of inertia. In current computer tomography scanners, the rotor is usually made to rotate by means of electric motors. However, these electric motors are only suitable for making the rotor rotate within a relatively long time prior to the examination and for maintaining a certain rotational speed by means of a control unit. However, on account of the large moment of inertia, it is not possible, or possible only to a slight but in no way sufficient extent, for the rotational speed of the rotor to be changed during acquisition of the image data. This would be possible only with considerably more powerful electric motors, although use thereof would have a highly disadvantageous effect on the size and price and thus on the efficiency of a computer tomography scanner.

By virtue of the fact that the position of the mass on the rotor can according to the invention be adjusted perpendicular to the rotation axis, the moment of inertia of the rotor as a whole can be changed. By changing the moment of inertia of a rotating object during its rotation, the rotational speed of the latter is changed at the same time on account of energy or the rotary momentum being retained. The rotational speed is reduced when the moment of inertia is increased, and is increased when the moment of inertia is reduced. In the computer tomography scanner according to the invention, this known physical effect is used to change the rotational speed of the rotor. If the position of the mass is moved away from the rotation axis, the moment of inertia is increased and the rotational speed of the rotor decreases. If the position of the mass is changed toward the rotation axis, the moment of inertia is reduced and the rotational speed of the rotor increases.

In respect of the invention, the term "mass" is to be understood in a very general manner. Firstly, it is to be understood as meaning solid bodies of any form, for example bodies made of metal, in particular having a high density such as lead. However, a liquid may also be used as the mass, said liquid being located for example in a chamber. By changing the shape of the chamber or by storing at least some of the liquid in a second chamber lying closer to or further away from the rotation axis, it is possible for the position of the liquid and thus of the mass to be changed. In respect of the term "position of the mass", the position of the center of gravity of the mass may of course also be used as an alternative.

In respect of the invention, the term "adjustment unit" is likewise to be understood in a very general manner. The position of a solid body can be fixed and changed on the rotor by many known means, said means usually being mechanical. Hereinafter, mention may therefore be made of only a few examples which nevertheless in no way restrict the scope of the term "adjustment unit". Electric, pneumatic or even hydraulic drives are conceivable. The movement of the solid body may be brought about by the rotation of a spindle drive, via a combination of toothed wheels and a toothed rack, or by means of a cable mechanism and a roller. If a liquid is used as the mass, its position can be changed by distributing it over various chambers by means of valves and pumps.

If the rotational speed is only to be reduced during the rotation, the mass may be brought into an inner position when the rotor is stationary and be held there by means of a stop. During operation, in order to reduce the rotational speed, the stop is released and then the mass, by virtue of centrifugal force, moves along a guide into an outer position where it meets a stop. When a liquid is used, this principle can be implemented in a similar manner by opening a valve, and the liquid located in an inner chamber then passes to an outer chamber by virtue of centrifugal force. On the other hand, with the embodiment as claimed in claim 2, the rotational speed of the rotor can be both increased and reduced during the rotation.

If just one mass with a variable position is arranged on the rotor and there are otherwise no movable parts attached to the rotor, there is no more than one position of the mass in which the common center of gravity of the rotor and the mass lies precisely on the rotation axis. In all the other positions, the common center of gravity lies next to the rotation axis, as a result of which a static unbalance arises. This unbalance is greater the further away the mass is from the balanced position. A static unbalance can be measured in a known manner when the rotor is stationary, and during rotation gives rise to a centrifugal force perpendicular to the rotation axis. This centrifugal force must be taken up and transmitted by the other components of the computer tomography scanner.

By virtue of the embodiment as claimed in claim 3, such a static unbalance can be avoided or at least almost eliminated independently of the distance of the masses from the rotation axis. The rotor is thus statically balanced with the masses at any rotational speed lying in the adjustment range. Corresponding dimensioning of the other components of the computer tomography scanner in order to take up centrifugal forces is no longer necessary.

In the embodiment as claimed in claim 4, in order to change the position of the masses, use is made of a device which is the same for all the masses. Moreover, the various traveling paths of the masses may be arranged in a symmetrical manner with respect to the rotation axis.

On the one hand, the rotational speed may be changed quasi-manually, for example by the user of the computer tomography scanner controlling the adjustment unit by means of a control unit and thus adjusting the position of the mass. However, as claimed in claim 5, it is possible for the user to define a different rotational speed during operation, which rotational speed is then set automatically by the control unit by correspondingly changing the position of the masses.

As mentioned above, for some medical applications it is advantageous if there is a certain ratio between the rotational speed and the heart rate of the patient. This ratio can be maintained automatically by the embodiment as claimed in claim 6. In addition, the control unit may be configured in such a way that a change in the heart rate can be predicted by certain parameters (for example characteristic points in an ECG) and the rotational speed is then adapted to provide for this.

Up to this point, it has been assumed that the rotor is at least almost balanced. However, this need not be the case, that is to say the rotor as such is not balanced. By way of example, there may be components of the CT device which are attached to the rotor and which, during operation, change their position with respect to the rotor. For example, there may be movable screens between the X-ray source and the examination area, by means of which screens the shape of the X-ray beam produced by the X-ray source can be set depending on the requirements of different applications. During rotation, an unbalance may also arise on account of the change in the position of such a component. An unbalance may also arise for example when a faulty component on the rotor is replaced and the replacement component does not have the same weight as the original component or has a different weight distribution. If these unbalances are static, they can be at least almost eliminated by the embodiment as claimed in claim 3. Moreover, the rotor as such need not be precisely balanced, and as a result a cost saving is made during manufacture.

Besides a static unbalance, the rotor may also have a so-called dynamic unbalance. As is known, a purely dynamic unbalance arises when the center of gravity of the rotor lies on the rotation axis but the main axis of inertia of the rotor does not coincide with the rotation axis. Purely dynamic unbalances arise only during operation, since the individual unbalance forces from the static point of view add up to zero. Purely dynamic unbalances manifest themselves in a bending moment (the so-called unbalance moment) along the rotation axis and usually give rise to periodically changing bearing loads.

A dynamic unbalance can be at least almost eliminated by the embodiment as claimed in claim 7. By moving one or more masses parallel to the rotation axis, as is known, the main axis of inertia of the rotor is rotated such that it lies on the rotation axis. The unbalance moment is then compensated by a countermoment. One or more additional masses may also be arranged on the rotor, the position of which masses can be changed only parallel to the rotation axis.

By virtue of the embodiment as claimed in claim 8, it is possible automatically to reduce or eliminate a static or a dynamic unbalance or both at the same time, prior to and/or during operation. The sensors used for this are generally known, for example from balancing machines for car wheels. No further details in this respect are thus given here.

The object is likewise achieved by the method as claimed in claims 9 and 10.

The invention will be further described with reference to examples of embodiments shown in the drawings to which, however, the invention is not restricted.

Figure 1:
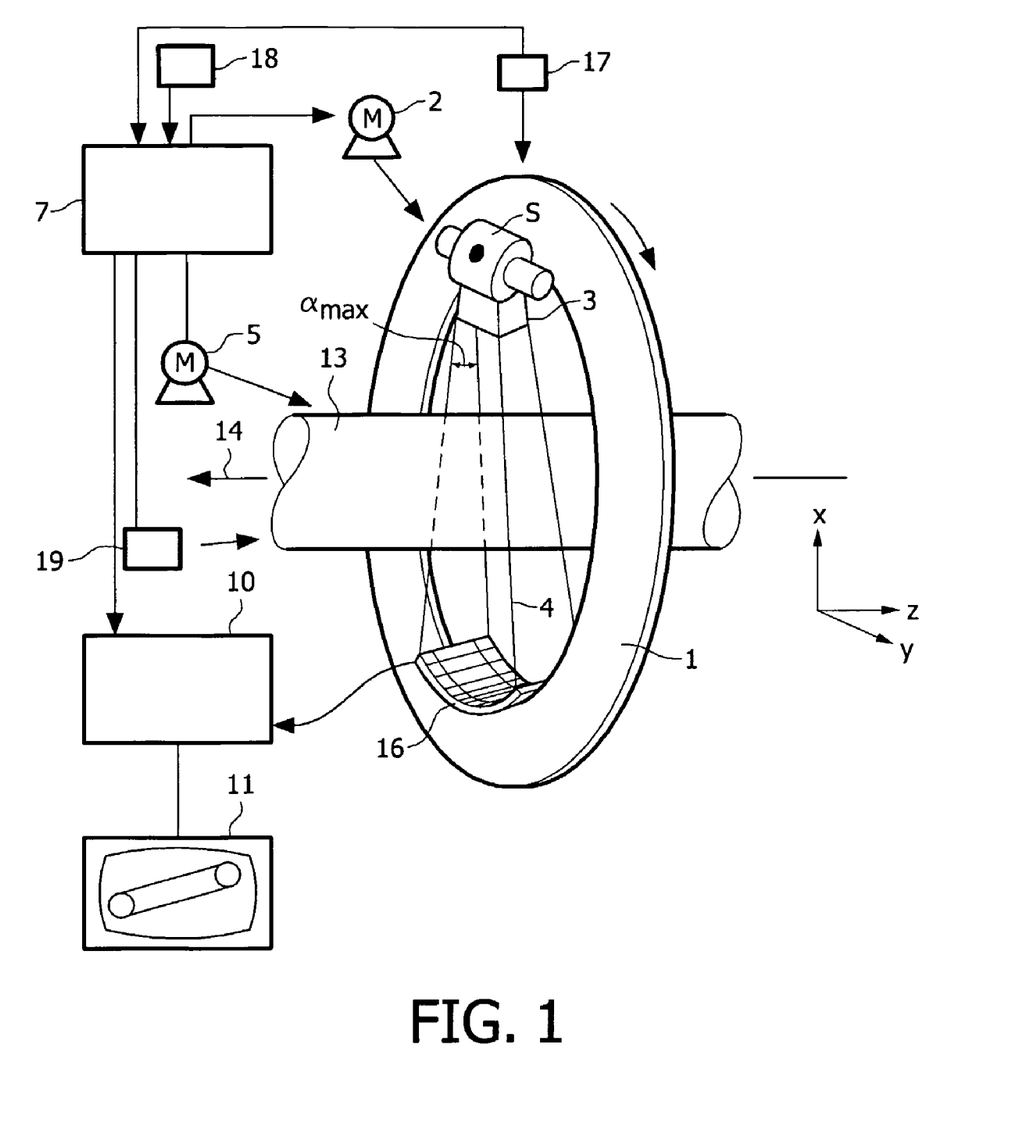
FIG. 1 schematically shows a computer tomography scanner according to the invention.

The computer tomography scanner shown in FIG. 1 may be used for example in medicine to produce slice images or volume images of patients or to examine luggage at airports. It comprises a gantry, the rotor 1 of which is shown schematically and can rotate about a rotation axis 14 which runs parallel to the z-direction. The rotor 1 is mounted in a stator 60, which stator for the sake of clarity is not shown in FIG. 1 but rather is shown separately in FIG. 6. Also not shown is a housing which has the shape of a flat tube and accommodates the rotor 1 and the stator 60. In order to rotate, the rotor 1 is driven by a motor 2 at a preferably constant but adjustable angular velocity. An angle sensor 17 detects the current angular position of the rotor 1. A radiation source S, for example an X-ray tube, is fixed on the rotor 1. Said radiation source is provided with a collimator arrangement 3 which forms a cone-shaped ray bundle 4 from the radiation produced by the radiation source S. The ray bundle 4 passes through a cylindrical examination area 13 in which an object may be located, for example a patient on a patient support table (both not shown) or else a technical object. Once it has passed through the examination area 13, the X-ray bundle 4 strikes a two-dimensional detector unit 16 which is fixed on the rotor 1. In addition or as an alternative, the detector unit 16 may also be configured such that the X-ray radiation scattered by the object is detected.

The opening angle $\alpha_{max}$ of the ray bundle 4 defines the diameter of the object cylinder within which the object to be examined is located during acquisition of the measured values. The opening angle is defined as the angle which a ray which lies in a plane perpendicular to the rotation axis 14 at the edge of the ray bundle 4 encloses with a plane defined by the radiation source S and the rotation axis 14. The examination area 13 or the object or patient support table may be moved parallel to the rotation axis 14 or to the z-axis by means of a motor 5. However, in a manner equivalent thereto, the gantry may also be moved in this direction. If the object is a technical object and not a patient, the object may be rotated during an examination, while the radiation source S and the detector unit 16 remain stationary.

When the motors 2 and 5 run at the same time, the radiation source S and the detector unit 16 describe a helical trajectory relative to the examination area 13. When, on the other hand, the motor 5 for advance in the direction of the rotation axis 14 is idle and the motor 2 is causing the rotor 1 to rotate, this results in a circular trajectory for the radiation source S and the detector unit 16 relative to the examination area 13.

The measured values acquired by the detector unit 16 are fed to a reconstruction computer 10 which is connected to the detector unit 16 for example via contactless data transmission (not shown). The reconstruction computer 10 reconstructs the CT image and displays it, for example on a monitor 11. The two motors 2 and 5, the reconstruction computer 10, the radiation source S and the transfer of the measured values from the detector unit 16 to the reconstruction computer 10 are controlled by a control unit 7. The control unit 7 may for example be a computer.

The electrical power required for operation of the components rotating on the rotor 1 is transmitted by slip rings (not shown).

Figure 2:
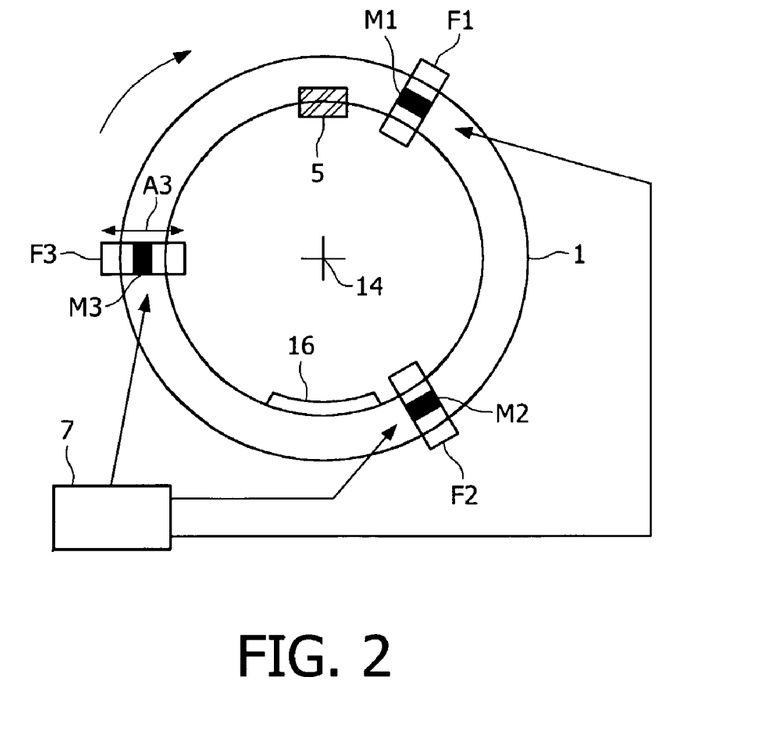
FIG. 2 shows the rotor of the computer tomography scanner.
Figure 3:
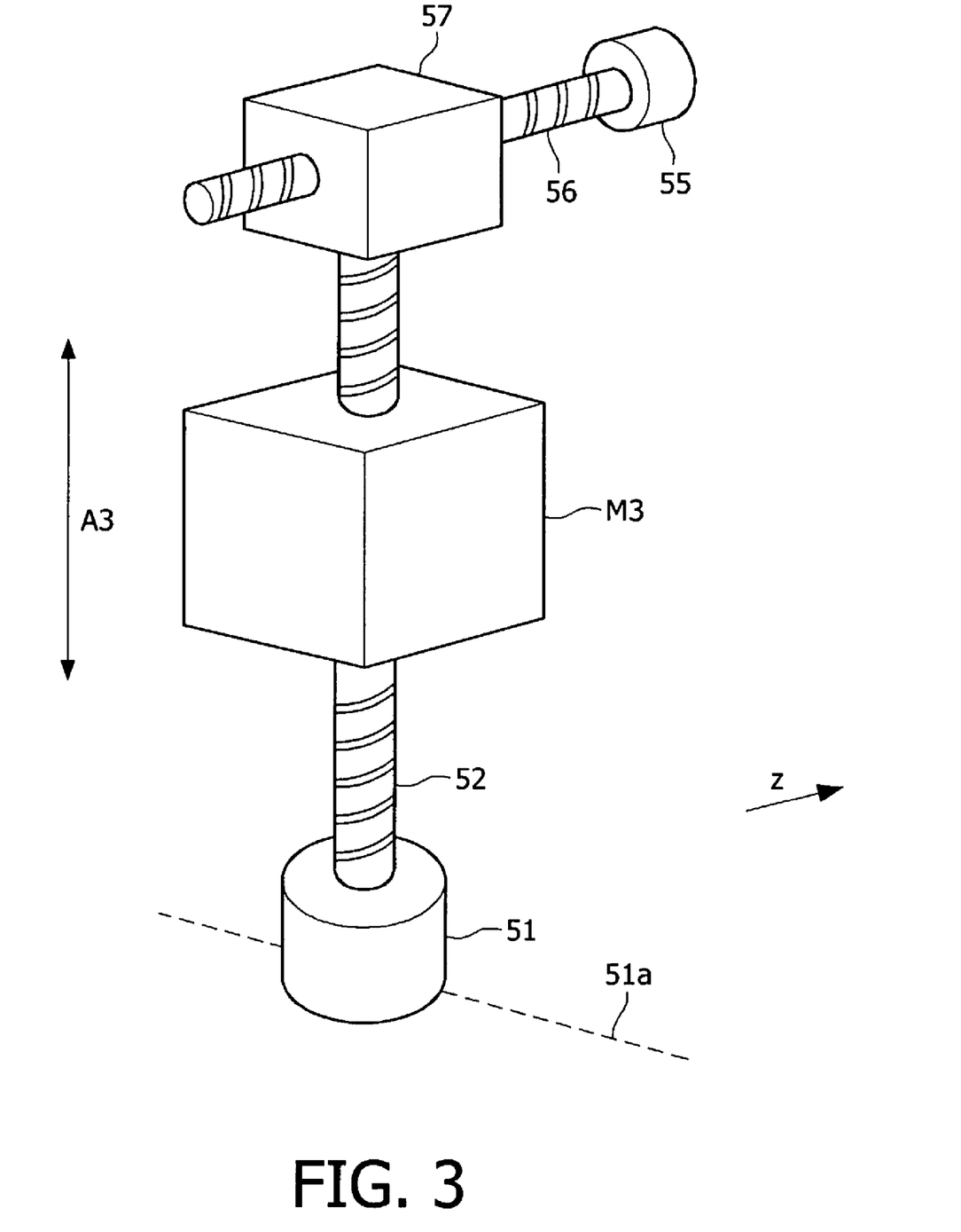
FIG. 3 shows an adjustable weight.

As shown schematically in FIG. 2, three masses in the form of weights M1, M2 and M3 are arranged on the rotor 1. The weights M1, M2 and M3 are each arranged in a guide F1, F2 and F3 such that they can be moved perpendicular to the rotation axis 14. FIG. 3 shows the weight M3 in greater detail. A motor 51 drives a spindle 52 in rotation. The spindle engages in a corresponding central hole of the weight M3 and together with the weight M3 forms a spindle drive. Depending on the direction of rotation of the spindle 52, the weight M3 moves toward the rotation axis 14 or away from it, as shown by the arrow A3. At the end opposite the motor 51, the spindle 52 is mounted in a bearing block 57 such that it can be rotated and pivoted. A second spindle drive is formed by a motor 55, a spindle 56 and the bearing block 57, wherein the axis of the spindle 56 forms an angle with the axis of the spindle 52. By rotating the spindle 56, the bearing block 57 and thus the weight M3 can be moved in the direction of the z-axis, that is to say parallel to the rotation axis 14. To this end, the motor 51 is mounted such that it can be tilted about the axis 51a. The motors 51 and 55 are controlled by the control unit 7.

Optionally, the connection between the weight M3 and the spindle 52 may be provided by a releasable catch (not shown), which is controlled for example by an electromagnet. If a sudden and rapid reduction in the rotational speed is required, this catch is released and the connection between the weight M3 and the spindle is broken. By virtue of the centrifugal force, the weight M3 moves away from the rotation axis until, depending on the installation position, it butts against either the bearing block 57 or the motor 51. A connection is then re-established between the weight M3 and the spindle 52 by virtue of the catch.

Figure 4:
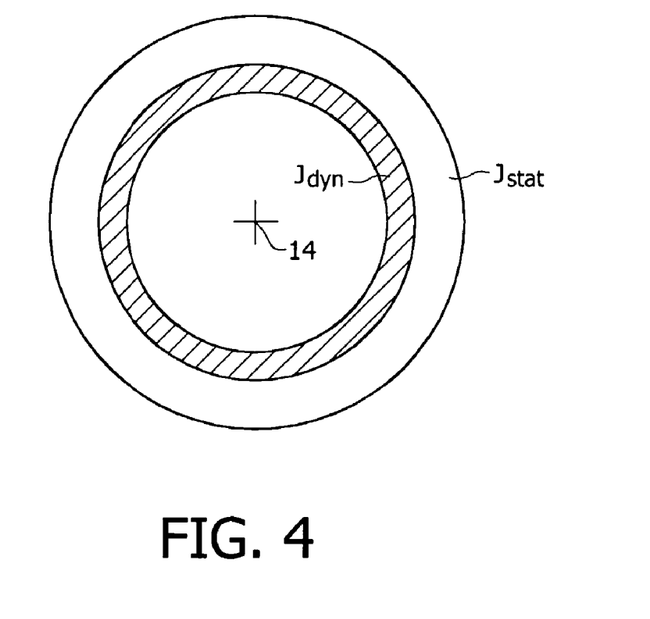
FIG. 4 shows a model for determining the moment of inertia of the rotor.

FIG. 4 shows a model which is used to carry out the following calculations given by way of example. The rotor without the weights M1, M2 and M3 has a mass of m=900 kg. In the model, it is simplified by a first hollow cylinder having an inner radius of $r_1$=570 mm and an outer radius of $r_2$=970 mm. The first cylinder has a moment of inertia $J_{stat}$. The weights M1, M2 and M3 together have a mass of 100 to 400 kg and are jointly simplified by a second hollow cylinder having a variable inner radius of $r_1$=70+/−15 mm and a variable outer radius of $r_2$=870+/−15 mm. This corresponds to a change in the position of the weights M1, M2 and M3 of in each case 15 mm toward the rotation axis and 15 mm away from the rotation axis with respect to a central starting position. The second hollow cylinder has a variable moment of inertia $J_{dyn}$.

Figure 5:
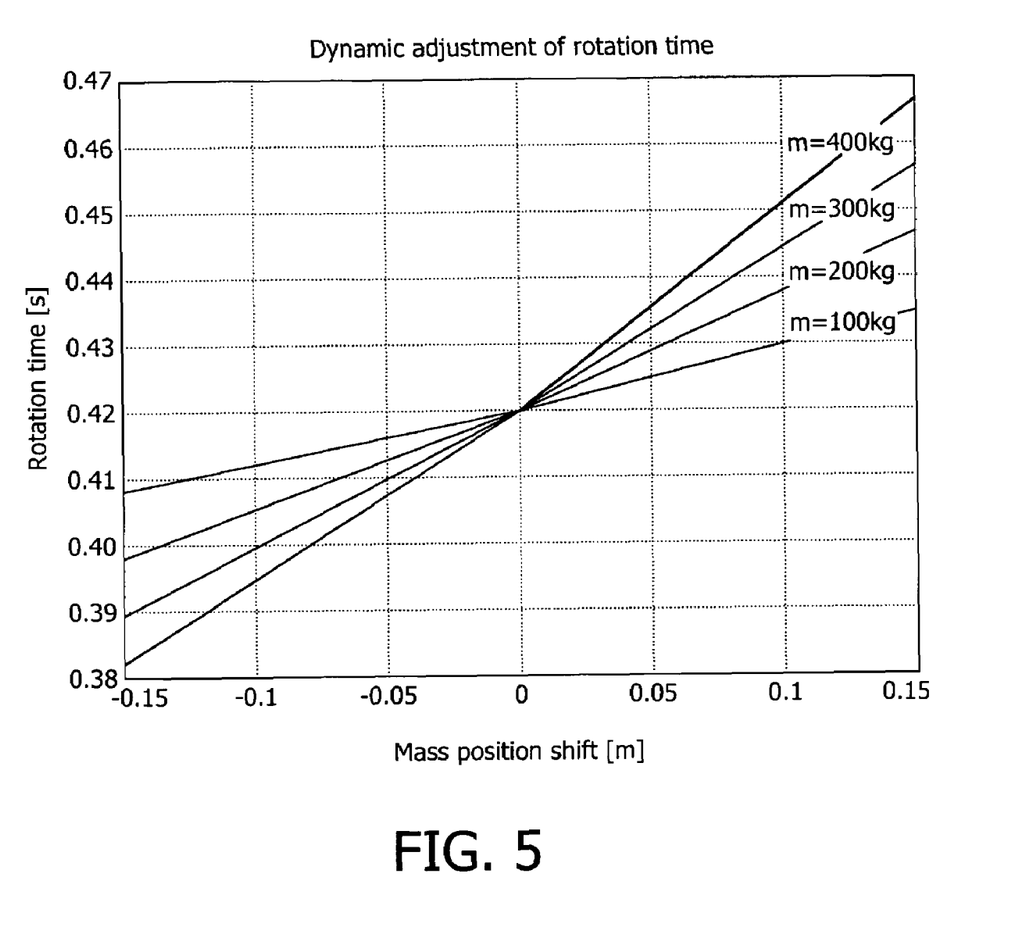
FIG. 5 shows a diagram which illustrates the rotation time of the rotor as a function of the weights and the distance of the weights from the rotation axis.

The moment of inertia of a hollow cylinder with respect to its longitudinal axis as rotation axis is generally calculated from $J=\frac{1}{2}m(r_2^2+r_1^2)$. The common moment of inertia of the weights M1, M2 and M3 and the rotor with respect to the rotation axis can be found from $J=J_{stat}+J_{dyn}$. On account of energy being retained, the rotary momentum of a rotating body is retained when its rotational speed or its moment of inertia changes. The rotary momentum L is usually calculated as $L=J\cdot\omega$, wherein $$\omega = 2\pi f = \frac{2\pi}{T}$$

at the rate of rotation f and the rotation time T. From the retention of the rotary momentum, $J_1T_2=J_2T_1$. FIG. 5 shows a diagram in which the change in rotational speed as a function of the change in position of the weights M1, M2 and M3 is illustrated for four different total weights from 100 kg to 400 kg. The rotation time of the rotor is shown on the vertical axis and the change in position of the weights is shown on the horizontal axis. For a total weight of the weights of 400 kg, for example, the original rotation time can be reduced from 0.42 s to 0.382 s by moving the weights M1, M2 and M3 15 mm away from the rotation axis, or can be increased to 0.468 s by moving the weights M1, M2 and M3 15 mm toward the rotation axis.

FIG. 1 also shows an operating unit 18 via which a user can select various medical applications for examining the patient. Applications are known which give particularly good results when the rate of rotation of the rotor 1 and the heart rate of the patient are in a certain ratio, that is to say an optimal ratio, to one another. If the user of the computer tomography scanner selects such an application, such a ratio is defined for the control unit 7. Using an ECG device 19, it is possible to detect inter alia the heart rate of a patient (not shown) who is located in the examination area 13. The control unit 7 compares the ratio of the detected heart rate to the actual rotational speed, which can be determined by means of the angle sensor 17. If the ratio is not correct, the weights M1, M2 and M3 are moved until the actual ratio corresponds to the predefined ratio.

For illustration purposes, reference should be made by way of example to the following publications from which the abovementioned ratios of rotational speed and heart rate are known: R. Manzke, et al. "Adaptive temporal resolution optimization in helical cardiac cone-beam CT reconstruction", Medical Physics, 30(12): pp. 3072-3080, 2003; M. Grass, et al. "Helical cardiac cone-beam reconstruction using retrospective ECG gating", Physics in Medicine and Biology, 48(18): pp. 3069-3084, 2003.

In these publications, algorithms are known which can be used to determine a mean temporal resolution as a function of rotational speed and heart rate. This relationship is shown by way of example in the diagram in FIG. 7. Said diagram shows the temporal resolution (vertical axis) as a function of the heart rate (horizontal axis in beats per minute). Curves can be seen for three different rotational speeds $T_{rot}$ of 0.33 s, 0.42 s and 0.50 s.

Figure 7:
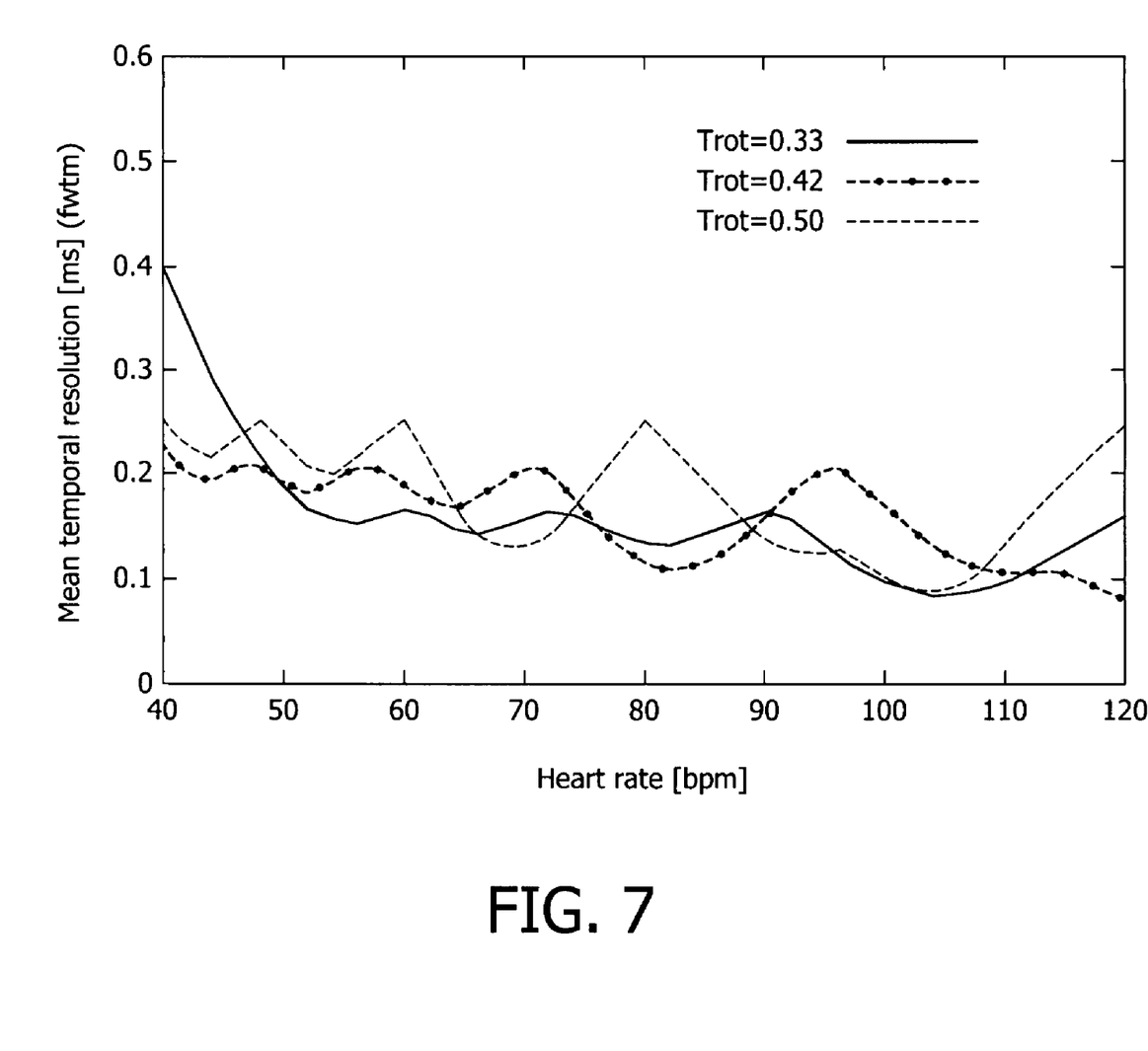
FIG. 7 shows a diagram which illustrates the relationship between resolution, heart rate and rotational speed.

The following is known from the abovementioned publications: the lower the temporal resolution, the better the result in terms of quality. At a rotational speed $T_{rot}$ of 0.42 s, unfavorable heart rates are accordingly obtained at the harmonics of the rotation time, e.g. 142.86 bpm, 95.24 bpm or 71.43 bpm. Favorable heart rates are obtained at decorrelated heart rates such as 114 bpm, 82 bpm or 64 bpm. In respect of the following example, for an optimal resolution the rotation time is 0.50 s and the heart rate is approximately 70 bpm. To improve the image contrast, a contrast agent is administered to the patient, as a result of which the heart rate increases to approximately 80 bpm. However, at this heart rate, the temporal resolution is considerably poorer. By increasing the rotational speed to approximately 0.42 s, an almost optimal resolution is once again obtained.

To this end, the curve data of the diagram of FIG. 7 are available to the control unit for example in the form of a look-up table. The control unit can deduce therefrom the rate of rotation which is most advantageous for each heart rate, and can set this rate of rotation as mentioned above by moving the weights.

In a further embodiment, the control unit 7 is also designed to predict a change in heart rate using known methods by appropriately evaluating the signals received from the ECG device 19, and to adapt the rotational speed just before the actual change.

In a further embodiment, the control unit 7 is also designed to detect any static and dynamic unbalances which arise, and as far as possible to eliminate them. Such an unbalance may arise during operation for example from the fact that the user of the computer tomography scanner would like to examine the examination object using a different application. To this end, it may be necessary to pivot the collimator arrangement 3 in order to change the shape of the cone-shaped ray bundle 4. An unbalance has nevertheless occurred on account of the changed position of the collimator arrangement 3 with respect to the rotor 1.

The stator 60 (shown in FIG. 6) of the computer tomography scanner stands with its four feet on the floor, only the feet 61, 62 and 63 being visible. A piezo element is arranged in each of the feet 61, 62 and 63. As is known, a piezo element outputs a corresponding electrical signal in the event of a change in pressure. These signals of the piezo elements arranged in the feet 61, 62 and 63 are detected and evaluated by the control unit 7. When the rotor 1 rotates in the stator 60, an unbalance of the rotor 1 is thus transmitted to the stator 60, as a result of which corresponding electrical signals are generated in the piezo elements. The piezo elements of the feet 61 and 62 generate a corresponding electrical signal if a static unbalance exists, and the piezo elements of the feet 62 and 63 generate a corresponding electrical signal in the event of a purely dynamic unbalance.

Figure 6:
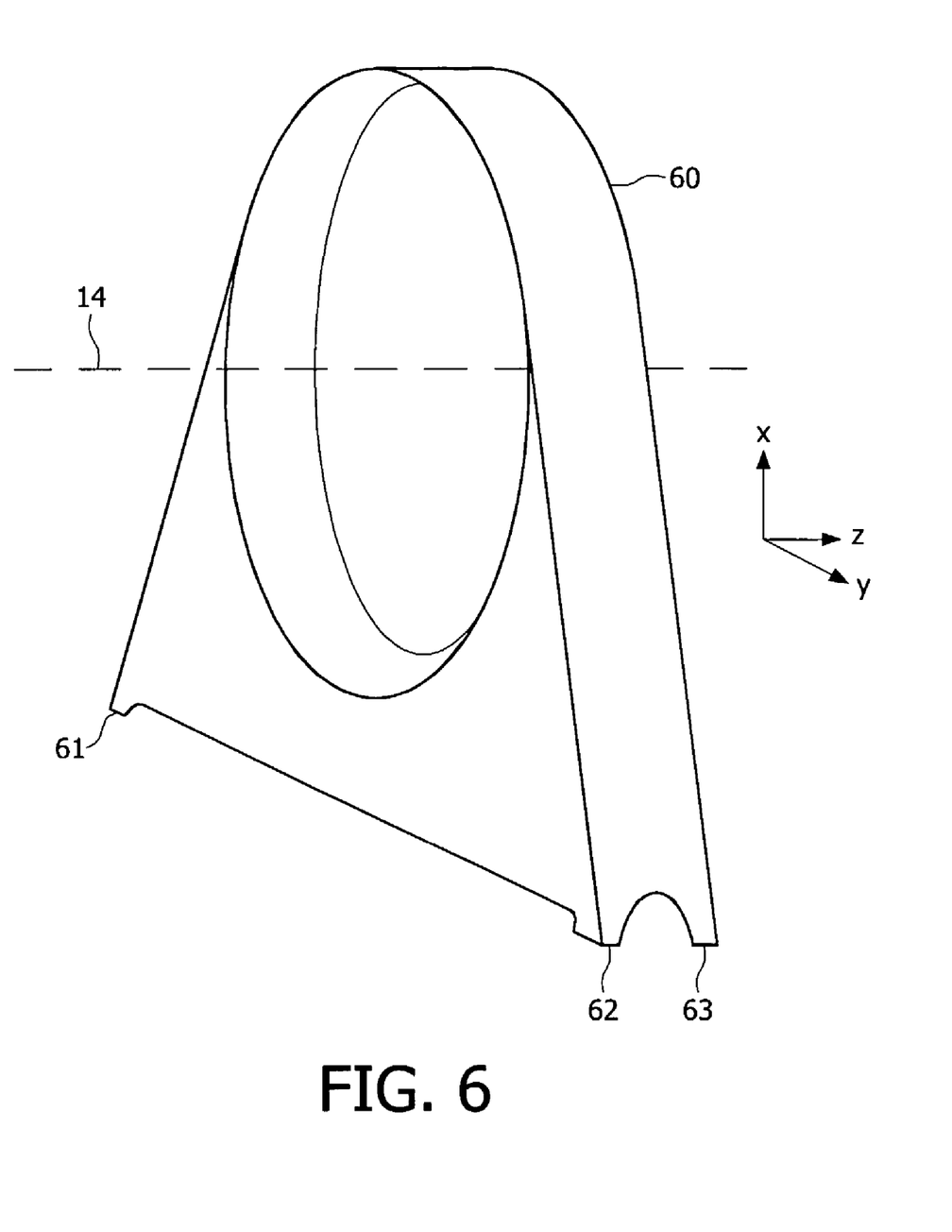
FIG. 6 shows the stator of the computer tomography scanner.

Based on the signals of the piezo elements and on the information from the angle sensor, the control unit 7 can calculate how the rotor has to be balanced, and will move the weights M1, M2 and M3 accordingly to compensate for a static and dynamic unbalance.

In order to detect static and dynamic unbalances in rotating systems, many possibilities using different sensors are known from mechanical engineering, and these can likewise be used in the computer tomography scanner according to the invention. The invention is therefore in no way restricted to the example mentioned above.

The invention claimed is:

1. A computer tomography scanner, comprising:
a rotor configured to rotate about a rotation axis,
at least one mass arranged on the rotor, and
an adjustment unit for changing the position of the mass perpendicular to the rotation axis during rotation of the rotor while scanning a subject.

2. The computer tomography scanner as claimed in claim 1, wherein the position of the mass can be changed toward the rotation axis and away from the rotation axis.

3. The computer tomography scanner as claimed in claim 1, comprising at least two masses, the respective positions of which can be changed in such a way that the common center of gravity of the masses and the rotor lies on the rotation axis.

4. The computer tomography scanner as claimed in claim 3, wherein the masses are of identical weight.

5. The computer tomography scanner as claimed in claim 1, comprising at least one sensor that measures a rotational speed of the rotor, and a control unit, which is coupled to the sensor and the adjustment unit, that controls the rotational speed of the rotor.

6. The computer tomography scanner as claimed in claim 5, comprising a device that measures a heart rate of the subject, wherein the control unit controls the rotational speed of the rotor in such a way that a predefinable ratio between the rotational speed and the measured heart rate is maintained.

7. The computer tomography scanner as claimed in claim 1, in which the position of at least one mass can be changed parallel to the rotation axis.

8. The computer tomography scanner as claimed in claim 1, comprising at least one sensor for measuring an unbalance of the rotor, and a control unit for positioning the mass or masses in such a way that the unbalance is reduced.

9. The computer tomography scanner of claim 1, wherein the adjustment unit rotates or pivots the mass.

10. The computer tomography scanner of claim 1, further including a device that measures a heart rate of the subject, and the adjustment unit changes the position of the mass to maintain a pre-defined ratio between the rotation speed and the measured heart rate.

11. The computer tomography scanner of claim 1, wherein the subject is one of a patient or luggage.

12. The method as claimed in claim 1, wherein changing the position of the mass changes the rotational speed of the rotor.

13. A method of changing the rotational speed of the rotor of a computer tomography scanner during rotation of the rotor about a rotation axis, comprising the following step:
changing the position of at least one mass arranged on the rotor perpendicular to the rotation axis during a scan of a subject.

14. The method as claimed in claim 13, comprising the following steps:
predefining a rotational speed,
detecting the actual rotational speed,
comparing the predefined rotational speed with the actual rotational speed,
changing the position of the mass in such a way that the actual rotational speed at least almost corresponds to the predefined rotational speed.

15. The method as claimed in claim 13, comprising the following step:
changing the position of at least one mass arranged on the rotor parallel to the rotation axis.

16. A computer tomography scanner, comprising:
a rotor configured to rotate about a rotation axis,
at least one mass arranged on the rotor, and
an adjustment unit configured to change a position of the mass on the rotor during rotation of the rotor while scanning a subject, thereby changing a rotation speed of the rotor while scanning the subject.

17. The computer tomography scanner of claim 16, wherein the mass is moved through a range of about fifteen millimeters towards the rotation axis to about fifteen millimeters away from the rotation axis with respect to a central starting position.

18. The computer tomography scanner of claim 16, further including a component that releases the mass from its position, wherein the mass freely moves in a direction away from the rotation axis when the mass is released and the rotor is rotating, and wherein the rotor decreases in rotation speed as the mass moves away from the rotation axis.

19. The computer tomography scanner of claim 16, wherein the rotation speed decreases from 0.42 seconds to 0.382 seconds.

20. The computer tomography scanner of claim 16, wherein the rotation speed increases from 0.42 seconds to 0.468 seconds.

* * * * *